(12) United States Patent
Rucker (10) Patent No.: US 8,425,412 B2
(45) Date of Patent: Apr. 23, 2013

(54) PAPILLA SPREADER

(75) Inventor: Brian K. Rucker, King, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1601 days.

(21) Appl. No.: 11/776,212

(22) Filed: Jul. 11, 2007

(65) Prior Publication Data

US 2008/0015416 A1      Jan. 17, 2008

Related U.S. Application Data

(60) Provisional application No. 60/830,835, filed on Jul. 14, 2006.

(51) Int. Cl.
*A61B 1/32* (2006.01)

(52) U.S. Cl.
USPC .......................................................... 600/214

(58) Field of Classification Search .................. 600/193, 600/206, 210, 214, 216, 217
See application file for complete search history.

(56) References Cited

U.S. PATENT DOCUMENTS

| | | | |
|---|---|---|---|
| 943,263 A | 12/1909 | Moraweck | |
| 1,510,416 A | 9/1924 | Pietz et al. | |
| 1,578,800 A | 3/1926 | Brandenberger | |
| 2,113,246 A | 4/1938 | Wappler | |
| 2,384,697 A | 9/1945 | Riccardi | |
| 2,968,041 A | 1/1961 | Skold | |
| 3,378,010 A | 4/1968 | Codling et al. | |
| 3,518,993 A | 7/1970 | Blake | |
| 3,616,497 A | 11/1971 | Esposito, Jr. | |
| 3,777,538 A | 12/1973 | Weatherly et al. | |
| 3,882,854 A | 5/1975 | Hulka et al. | |
| 3,958,576 A | 5/1976 | Komiya | |
| 4,038,987 A | 8/1977 | Komiya | |

(Continued)

FOREIGN PATENT DOCUMENTS

| | | |
|---|---|---|
| DE | 23 30182 | 6/1973 |
| DE | 19534320 | 2/1997 |

(Continued)

OTHER PUBLICATIONS

Office Action for Canadian Patent Application No. 2,659,591 mailed Aug. 17, 2010, 2 pgs.

(Continued)

*Primary Examiner* — Kevin T Truong
*Assistant Examiner* — Michael Araj
(74) *Attorney, Agent, or Firm* — Brinks Hofer Gilson & Lione (57) ABSTRACT

The present invention provides apparatus and methods for facilitating entry through a bodily opening comprising a spreader having a plurality of arms, each of the arms being formed of a resilient material and shaped so that the distal ends tend to be spaced apart from each other when the spreader is in an open position. At least one of the arms has an engaging member having a sharpness adapted to grasp tissue. When the spreader is radially deployed to the open position, the engaging member grasps tissue adjacent the bodily opening and urges the tissue away from the opening to facilitate visualization of the opening and/or access into the opening. A catheter or other device may subsequently be inserted between one or more arms of the spreader and through the bodily opening while the spreader holds the tissue in a spread position.

15 Claims, 11 Drawing Sheets

U.S. PATENT DOCUMENTS

| | | | |
|---|---|---|---|
| 4,046,149 A | 9/1977 | Komiya | |
| 4,169,476 A | 10/1979 | Hiltebrandt | |
| 4,215,871 A | 8/1980 | Hirsch et al. | |
| 4,367,746 A | 1/1983 | Derechinsky | |
| 4,394,861 A | 7/1983 | Sciortino | |
| 4,394,864 A | 7/1983 | Sandhaus | |
| 4,446,865 A | 5/1984 | Jewusiak | |
| 4,485,817 A | 12/1984 | Swiggett | |
| 4,496,090 A | 1/1985 | Crevier et al. | |
| 4,512,345 A | 4/1985 | Green | |
| 4,681,107 A | 7/1987 | Kees, Jr. | |
| 4,706,668 A | 11/1987 | Backer | |
| 4,714,075 A | 12/1987 | Krauter et al. | |
| 4,735,194 A | 4/1988 | Stiegmann | |
| 4,759,364 A | 7/1988 | Boebel | |
| 4,796,627 A | 1/1989 | Tucker | |
| 4,821,721 A | 4/1989 | Chin et al. | |
| 4,835,824 A | 6/1989 | Durham et al. | |
| 4,841,888 A | 6/1989 | Mills et al. | |
| 4,880,015 A | 11/1989 | Nierman | |
| 4,887,612 A | 12/1989 | Esser et al. | |
| 4,934,364 A | 6/1990 | Green | |
| 4,945,920 A | 8/1990 | Clossick | |
| 4,971,067 A | 11/1990 | Bolduc et al. | |
| 4,983,176 A | 1/1991 | Cushman et al. | |
| 5,015,249 A | 5/1991 | Nakao et al. | |
| 5,049,153 A | 9/1991 | Nakao et al. | |
| 5,062,848 A | 11/1991 | Frazee et al. | |
| 5,100,418 A | 3/1992 | Yoon et al. | |
| 5,112,343 A | 5/1992 | Thornton | |
| 5,156,609 A | 10/1992 | Nakao et al. | |
| 5,222,961 A | 6/1993 | Nakao et al. | |
| 5,242,456 A | 9/1993 | Nash et al. | |
| 5,300,081 A | 4/1994 | Young et al. | |
| 5,304,183 A | 4/1994 | Gourlay et al. | |
| 5,366,459 A | 11/1994 | Yoon | |
| 5,395,381 A | 3/1995 | Green et al. | |
| 5,403,342 A * | 4/1995 | Tovey et al. | 606/205 |
| 5,441,509 A | 8/1995 | Vidal et al. | |
| 5,445,167 A | 8/1995 | Yoon et al. | |
| 5,464,416 A | 11/1995 | Steckel | |
| 5,474,567 A | 12/1995 | Stefanchik et al. | |
| 5,486,185 A | 1/1996 | Freitas et al. | |
| 5,514,148 A | 5/1996 | Smith, III | |
| 5,527,319 A | 6/1996 | Green et al. | |
| 5,540,124 A | 7/1996 | Srhoj | |
| 5,569,274 A | 10/1996 | Rapacki et al. | |
| 5,601,574 A | 2/1997 | Stefanchik et al. | |
| 5,609,601 A * | 3/1997 | Kolesa et al. | 606/170 |
| 5,634,932 A | 6/1997 | Schmidt | |
| 5,695,504 A | 12/1997 | Gifford, III et al. | |
| 5,700,271 A | 12/1997 | Whitfield et al. | |
| 5,733,329 A | 3/1998 | Wallace et al. | |
| 5,766,184 A | 6/1998 | Matsuno et al. | |
| 5,766,189 A | 6/1998 | Matsuno | |
| 5,782,747 A | 7/1998 | Zimmon | |
| 5,895,394 A | 4/1999 | Kienzle et al. | |
| 5,980,534 A | 11/1999 | Gimpelson | |
| 5,989,268 A | 11/1999 | Pugsley, Jr. et al. | |
| 6,001,110 A | 12/1999 | Adams | |
| RE36,720 E | 5/2000 | Green et al. | |
| 6,139,555 A | 10/2000 | Hart et al. | |
| 6,155,968 A | 12/2000 | Wilk | |
| 6,167,605 B1 | 1/2001 | Morales | |
| 6,193,733 B1 | 2/2001 | Adams | |
| 6,228,023 B1 * | 5/2001 | Zaslavsky et al. | 600/204 |
| 6,267,776 B1 | 7/2001 | O'Connell | |
| 6,350,269 B1 | 2/2002 | Shipp et al. | |
| 6,352,541 B1 | 3/2002 | Kienzle et al. | |
| 6,464,710 B1 | 10/2002 | Foster | |
| 6,814,742 B2 | 11/2004 | Kimura et al. | |
| 2001/0049497 A1 | 12/2001 | Kalloo et al. | |
| 2002/0032462 A1 | 3/2002 | Houser et al. | |
| 2002/0045909 A1 | 4/2002 | Kimura et al. | |
| 2002/0055750 A1 | 5/2002 | Durgin et al. | |
| 2002/0062130 A1 | 5/2002 | Jugenheimer et al. | |
| 2002/0128667 A1 | 9/2002 | Kobayashi et al. | |
| 2002/0133178 A1 | 9/2002 | Muramatsu et al. | |
| 2002/0138083 A1 | 9/2002 | Muramatsu et al. | |
| 2002/0138085 A1 | 9/2002 | Muramatsu et al. | |
| 2002/0151916 A1 | 10/2002 | Muramatsu et al. | |
| 2002/0173805 A1 | 11/2002 | Matsuno et al. | |
| 2003/0069592 A1 | 4/2003 | Adams et al. | |
| 2003/0069593 A1 | 4/2003 | Tremulis et al. | |
| 2004/0092978 A1 | 5/2004 | Surti | |
| 2005/0033312 A1 | 2/2005 | Suzuki | |
| 2005/0143767 A1 | 6/2005 | Kimura | |

FOREIGN PATENT DOCUMENTS

| | | |
|---|---|---|
| DE | 298 11 510 | 6/1998 |
| DE | 100 11 292 | 8/2000 |
| DE | 19955614 | 7/2001 |
| DE | 102 11 049 | 3/2002 |
| EP | 0 738 501 | 10/1996 |
| EP | 1325717 | 7/2003 |
| EP | 1493392 | 1/2005 |
| EP | 1604614 | 12/2005 |
| JP | 63-160644 | 1/1990 |
| WO | WO 99/20183 | 4/1999 |
| WO | WO 00/21443 | 4/2000 |
| WO | WO 03/030746 | 4/2003 |

OTHER PUBLICATIONS

International Preliminary Report on Patentability for PCT/US2007/015803 issued Jan. 14, 2009, 9 pgs.
Office Action for European Patent Application No. 07 810 342.1 mailed Jun. 30, 2010, 3pgs.
Response to Office Action for European Patent Application No. 07 810 342.1 filed Oct. 29, 2010, 14 pgs.
Partial International Search Report for PCT/US07/12754 dated Dec. 11, 2007.
International Search Report for PCT Application No. PCT/US03/11496 dated Jul. 11, 2003.
International Search Report for PCT Application No. PCT/US03/11820 dated Jul. 11, 2003.
International Search Report for PCT Application No. PCT/US07/15803 dated Mar. 7, 2008.
Examiner's First Report on Australian Patent Application No. 2007272981 dated Mar. 28, 2012, 2 pgs.
Office Action for Japanese Patent Application No. 2009-520764 sent May 30, 2012, 5 pgs.
Response to Office Action for Canadian Patent Application No. 2,659,591 filed Feb. 8, 2011, 8 pgs.
Voluntary Amendment for Canadian Patent Application No. 2,659,591 filed Apr. 4, 2011, 3 pgs.
Notice of Allowance for Canadian Patent Application No. 2,659,591 dated Nov. 30, 2011, 1 pg.
Registration/Entitlement for Canadian Patent Application No. 2,659,591 dated Jun. 11, 2012, 1 Pg.
Decision to Grant European Patent Application No. 07 810 342.1 dated Feb. 2, 2012, 2 pgs.

* cited by examiner

PAPILLA SPREADER

PRIORITY CLAIM

This invention claims the benefit of priority of U.S. Provisional Application Ser. No. 60/830,835, entitled "Papilla Spreader," filed Jul. 14, 2006, the disclosure of which is hereby incorporated by reference in its entirety.

TECHNICAL FIELD

The present invention relates to apparatus and methods for facilitating entry into a bodily opening, and more specifically, to a device that can be used to grasp tissue around the bodily opening and spread the tissue apart to facilitate entry into the opening.

BACKGROUND INFORMATION

There are many instances in which it is surgically desirable or necessary to obtain access through a constrained bodily opening. For example, it may become desirable to access a patient's common bile duct to remove a gallstone or treat a biliary stricture. In order to access the common bile duct, an endoscopic retrograde cholangiopancreatography (ERCP) procedure may be performed, in which a physician inserts an endoscope into a patient's mouth, through the esophagus, stomach, and into the duodenum. The endoscope may comprise a working lumen through which a wire guide, catheter and/or other device may be loaded. Such devices may be guided, via the working lumen of the endoscope, into the duodenum, through the papilla of Vater, and then into the common bile duct.

There are several problems that may be encountered when advancing a wire guide or other device through the papilla of Vater and into the common bile duct. First, the insertion of the wire guide may be rendered difficult due to folds of soft tissue in the vicinity of the papillar opening, i.e., the folds of tissue may partially or fully block or impede access through the opening. Further, it may be difficult to achieve the proper angle necessary to gain entry from the duodenum into the common bile duct. If the proper angle is not achieved, an errant wire guide entry may cause damage to the relatively sensitive pancreatic duct.

One known technique for facilitating access into the common bile duct during an ERCP procedure is performing a sphincterectomy at the sphincter of Oddi. Several drawbacks are associated with sphincterectomies. For example, cutting the sphincter may lead to bleeding and acute pancreatitis. Further, an endoscopic sphincterectomy permanently destroys the sphincter of Oddi, thus exposing the biliary tree to the risk of future infection.

In view of the drawbacks of previously-known techniques, there is a need for a device that facilitates access into an anatomical opening while reducing the likelihood of damaging a patient's anatomy.

SUMMARY

The present invention provides apparatus and methods for facilitating entry through a bodily opening, such as the papilla of Vater. The apparatus comprises a spreader having a plurality of arms, each of the arms having proximal and distal ends. The proximal end of each arm is joined at a proximal region of the spreader and extends distally therefrom. Each of the arms are formed of a resilient material and shaped so that the distal ends tend to be spaced apart from each other when the spreader is in an open position and adjacent to each other when the spreader is in a closed position.

At least one engaging member is disposed near the distal end of each arm. Each engaging member has a shape and configuration adapted to grasp tissue. When the spreader is transformed from the closed position to the open position, the engaging member is adapted to grasp tissue in the vicinity of the bodily opening and spread the tissue in a direction away from the bodily opening. When the tissue is moved away from the opening, improved visualization and/or access into the bodily opening may be achieved.

In one embodiment, the spreader is delivered to a target site using a catheter having proximal and distal ends and a first lumen disposed therebetween. The first lumen is adapted to receive the spreader and constrain the arms of the spreader in the closed position. The catheter may be proximally retracted with respect to the arms of the spreader to permit the arms to assume a predetermined expanded configuration in the open position. If desired, while the spreader engages and spreads the tissue in a direction away from the bodily opening, the catheter may be advanced between at least two of the arms of the spreader and through the bodily opening.

In order to remove the spreader, the catheter may be distally advanced over the proximal region of the spreader and over each of the arms. The spreader is transformed from the open position to the closed position in which the arms are radially constrained by the catheter, causing a weakened engagement between the spreader and the tissue. Alternatively, the spreader may be left inside the patient after the procedure.

In order to ensure controlled deployment of the spreader, the apparatus may comprise first and second retainers. The second retainer is adapted to be coupled to the first retainer prior to deployment of the spreader, and further configured to be disengaged from the first retainer after the spreader is deployed. In some embodiments, the first and second retainers are adapted to be re-engaged with each other to capture and retrieve the spreader.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patent's anatomy during a medical procedure.

The present invention provides apparatus suitable for spreading tissue, such as soft tissue in the vicinity of a bodily opening, passageway or cavity, to facilitate access into the opening. In a preferred embodiment, the apparatus comprises a spreader that is configured to engage tissue. The spreader has a constrained delivery state, and an unconstrained state in which a plurality of arms deploy in a radially outward direction to engage tissue and urge the tissue in a direction away from the opening.

Figure 1A:
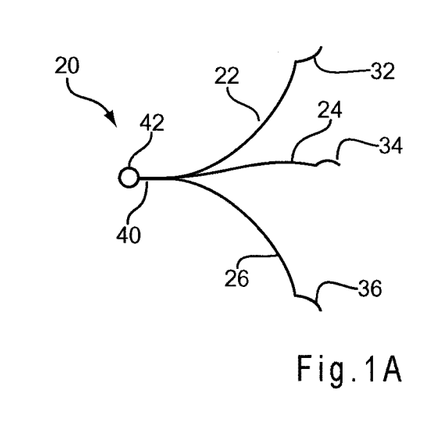
FIGS. 1A-1B are, respectively, side and front views illustrating one embodiment of a spreader according to the present invention.
Figure 1B:
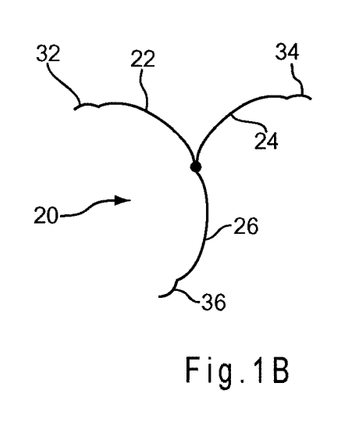

Referring to FIGS. 1A-1B, a first embodiment of a spreader according to the present invention is shown. Spreader 20 comprises proximal region 40 and plurality of arms 22, 24 and 26 extending from proximal region 40. Plurality of arms 22, 24 and 26 may be independently manufactured and then joined together at proximal region 40, or may be integrally formed during manufacture. While three arms are preferred, it is contemplated that greater or fewer than three arms may be used.

Plurality of arms 22, 24 and 26 comprise engaging members 32, 34 and 36, respectively, which preferably are outwardly bent to facilitate grasping of tissue, as explained in greater detail below. Engaging members 32, 34 and 36 may be integrally formed with arms 22, 24 and 26, or may comprise sharpened members that are attached to distal regions of one or more arms 22, 24 and 26.

Spreader 20 may be made from any suitable resilient material such as stainless steel, nitinol, plastic, and the like. In addition, arms 22, 24 and 26 may have a cross-sectional shape that is round, square, triangular, pie-shaped, truncated cone, and the like.

Spreader 20 may comprise a retainer system to ensure controlled deployment. A first retainer, such as looped region 42 of FIG. 1A, may be integrally formed with proximal region 40 or separately attached thereto. The first retainer preferably is provided with a shape that will complement a shape provided on a second retainer of a delivery/deployment system so that the first and second retainers will matingly join with each other. As will be explained in greater detail below, by coupling the first and second retainers together, controlled deployment of spreader 20 may be achieved.

Figure 2A:
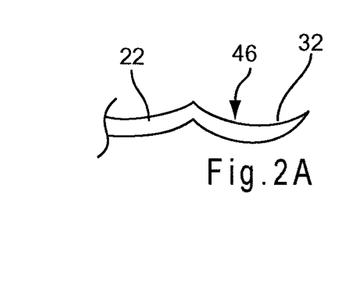
FIGS. 2A-2C are side views illustrating alternative designs of an engaging member of the spreader of FIGS. 1A-1B.
Figure 2B:
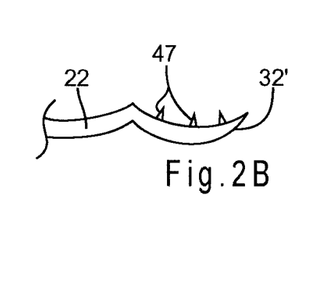
Figure 2C:
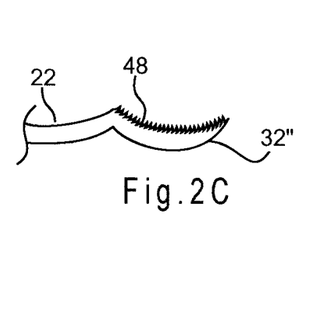

Referring now to FIGS. 2A-2C, various engaging members suitable for spreader 20 are described. In FIG. 2A, engaging member 32 comprises a curved region 46, which is curved in an outward direction as shown. In FIG. 2B, engaging member 32' comprises one or more barbs 47, which may be disposed on curved region 46 and adapted to grasp tissue. In FIG. 2C, engaging member 32" comprises roughened surface 48, which may be formed integral to curved region 46 and adapted to grasp tissue. While various embodiments of engaging member 32 have been depicted, engaging members 34 and/or 36 of spreader 20 also may comprise any of the features shown in FIGS. 2A-2C.

Figure 3:
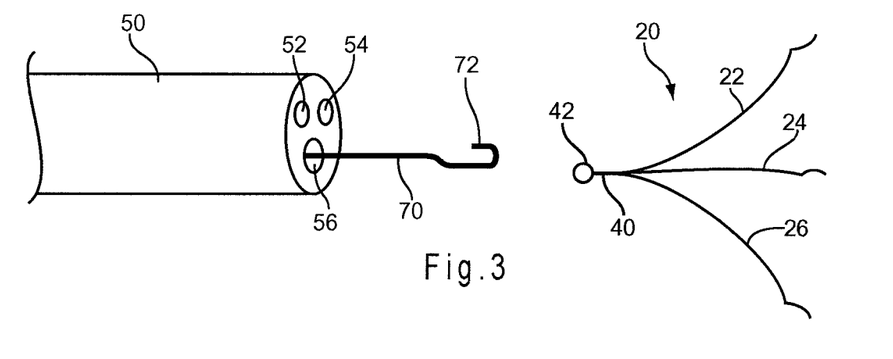
FIG. 3 illustrates a catheter and retainer system that may be used to deploy the spreader of FIGS. 1A-1B.

Referring now to FIG. 3, a catheter and first retainer system that may be used to deploy spreader 20 are described. Catheter 50 comprises proximal and distal ends and at least one lumen extending therebetween. In the embodiment of FIG. 3, catheter 50 has three lumens 52, 54 and 56. Lumen 56 is configured to receive, deliver and facilitate deployment of spreader 20, as explained in greater detail below. The other lumen(s) may be adapted to perform other auxiliary functions, such as receiving a wire guide, an extraction basket adapted to remove a stone, a lithotripsy basket adapted to disintegrate a stone, a balloon catheter adapted to treat a biliary stricture, and/or other devices. The other lumen(s) may also be adapted for the passage of fluids, such as the delivery of contrast. The distal region of catheter 50 also may comprise an external balloon (not shown), which is adapted to be selectively inflated, for example, to treat a biliary stricture.

Catheter 50 preferably comprises a flexible, tubular member that may be formed from one or more semi-rigid polymers. For example, catheter 50 may be manufactured from polyurethane, polyethylene, tetrafluoroethylene, polytetrafluoroethylene, perfluoalkoxl, fluorinated ethylene propylene, or the like. The catheter may have a length and an outer diameter sufficient to extend through a working channel of conventional endoscope 110 (see FIGS. 7A-7C). For example, catheter 50 may comprise an outer diameter of about 6 to 7 French in order to fit within the working channel. Catheter 50 also may comprise a hydrophilic coating overlying its outer surface. The hydrophilic coating, when applied to the outer surface of catheter 50, imparts suppleness and kink resistance to the catheter. The hydrophilic coating also may provide a lubricated surface to facilitate movement through the working channel of endoscope 110.

In the embodiment of FIG. 3, the first retainer of the retainer system is in the form of a looped region 42 at proximal region 40 of spreader 20. The second retainer adapted for use with spreader 20 is in the form of wire 70 having proximal and distal ends and hook member 72 disposed at the distal end. Hook member 72 may be integrally formed at the distal end of wire 70 or attached thereto Hook member 72 is adapted to be disposed through looped region 42 of spreader 20. When spreader 20 and wire 70 are disposed within lumen 56, hook member 72 is disposed through looped region 42 and arms 22, 24 and 26 are in a closed position at a location distal to wire 70. In the closed position, arms 22, 24 and 26 are adjacent to one another and held in a constrained state within the confines of lumen 56.

As will be explained in greater detail below, catheter 50 may be retracted proximally with respect to wire 70 and spreader 20, thereby exposing arms 22, 24 and 26 and causing the arms to assume a predetermined, radially expanded open position, as shown in FIG. 3. Further, when catheter 50 is proximally retracted past hook member 72, the coupling junction where looped region 42 is coupled to hook member 72 is exposed, allowing spreader 20 to be released from wire 70.

Figure 4:
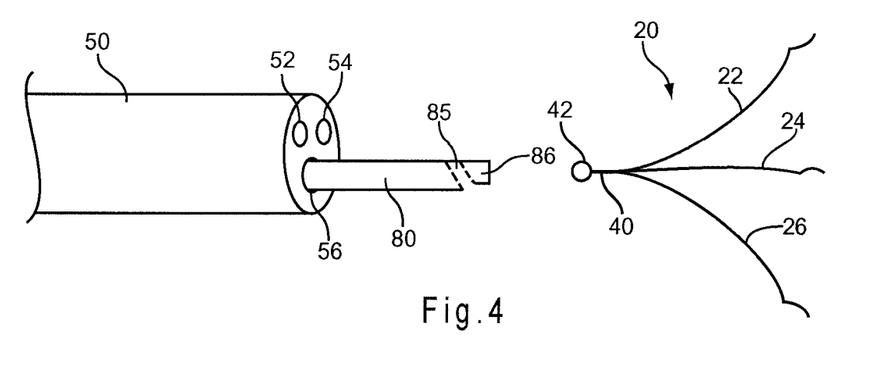
FIG. 4 illustrates a catheter and alternative retainer system that may be used to deploy the spreader of FIGS. 1A-1B.

Referring now to FIG. 4, an alternative retainer system, which may be used to deploy spreader 20, is described. In FIG. 4, the second retainer comprises rod 80 having proximal and distal ends and bore 85 disposed at least partially through rod 80 near the distal end. Rod 80 is configured to be disposed within lumen 56 and is adapted for longitudinal movement therein. Rod 80 may comprise any suitable material, such as stainless steel.

Bore 85 is adapted to receive looped region 42 of spreader 20. More specifically, looped region 42 is sufficiently flexible to allow lateral compression so as to fit in bore 85. Bore 85 may extend partially or completely through rod 80, and preferably is angled to accommodate looped region 42, as shown in FIG. 4. In a preferred embodiment, rod 80 comprises reduced diameter region 86, which may be formed distal to bore 85 and transition into bore 85, as shown in FIG. 4. When looped region 42 is disposed within bore 85, proximal region 40 of spreader 20 is aligned beneath (adjacent to) reduced diameter region 86, so that the overall radial profile of the apparatus is not increased. Further, when arms 22, 24 and 26 are in the closed position at a location distal to rod 80, the overall radial profile of the constrained arms is preferably about the same as the outer diameter of rod 80. Therefore, the constrained arms do not substantially increase the radial delivery profile of the apparatus.

As will be explained in greater detail below, catheter 50 may be retracted proximally with respect to wire 80 and spreader 20, thereby exposing arms 22, 24 and 26 and causing the arms to assume their predetermined, radially expanded open position, as shown in FIG. 4. Further, when catheter 50 is proximally retracted past bore 85, the coupling junction where looped region 42 is coupled to rod 80 is exposed, allowing spreader 20 to be released from rod 80.

Figure 5:
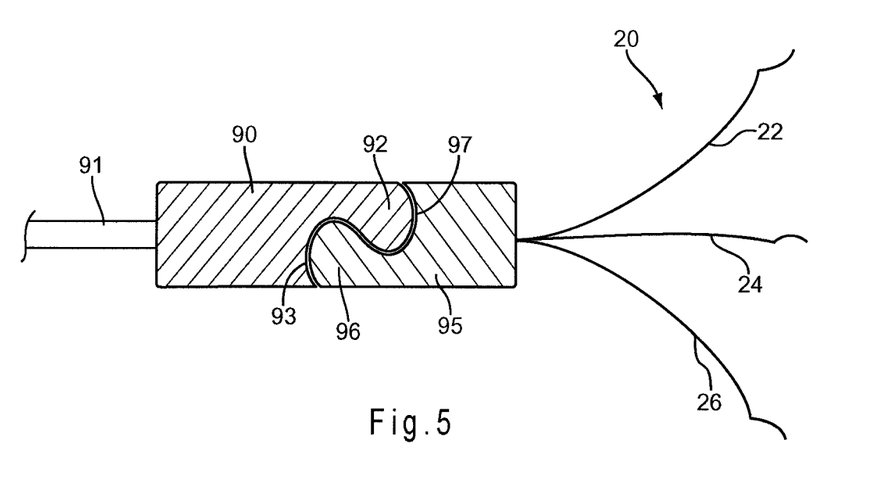
FIG. 5 illustrates a further alternative retainer system that may be used to deploy the spreader of FIGS. 1A-1B.

Referring now to FIG. 5, an alternative retainer system, which may be used to deploy spreader 20, is described. First retainer 95 is operably attached to arms 22, 24 and 26 of spreader 20. A proximal end of second retainer 90 is attached to operating wire 91, as shown in FIG. 5. First retainer 95 and second retainer 90 preferably are cylindrical in cross-sectional shape and have substantially identical outer diameters when mating, as described below.

First retainer 95 comprises partially rounded notch 97 formed therein, and has rounded knob 96 formed proximal to notch 97. Similarly, second retainer 90 comprises partially rounded notch 93 formed therein, and has rounded knob 92 disposed distal to notch 93. During delivery of the device, rounded knob 92 is aligned with notch 97, while rounded knob 96 is aligned with notch 93, as shown in FIG. 5, thereby securing first retainer 95 to second retainer 90. In this embodiment, the first and second retainers are matingly held together when disposed within the confines of catheter lumen 56, thereby inhibiting movement of the retainers with respect to each other. When a distal end of catheter 50 is retracted proximally past first retainer 95 and second retainer 90, the coupling region between the retainers is exposed, and since the retainers are no longer radially constrained, they will releasably detach from one another.

While FIGS. 3-5 illustrate two exemplary retaining systems that may be used to deliver spreader 20, many other retaining systems may be provided. For example, the first and second retainers may be provided in accordance with any of the retainer mechanisms described in U.S. patent application Ser. No. 11/807,827, filed May 30, 2007, which is hereby incorporated by reference in its entirety.

Figure 6:
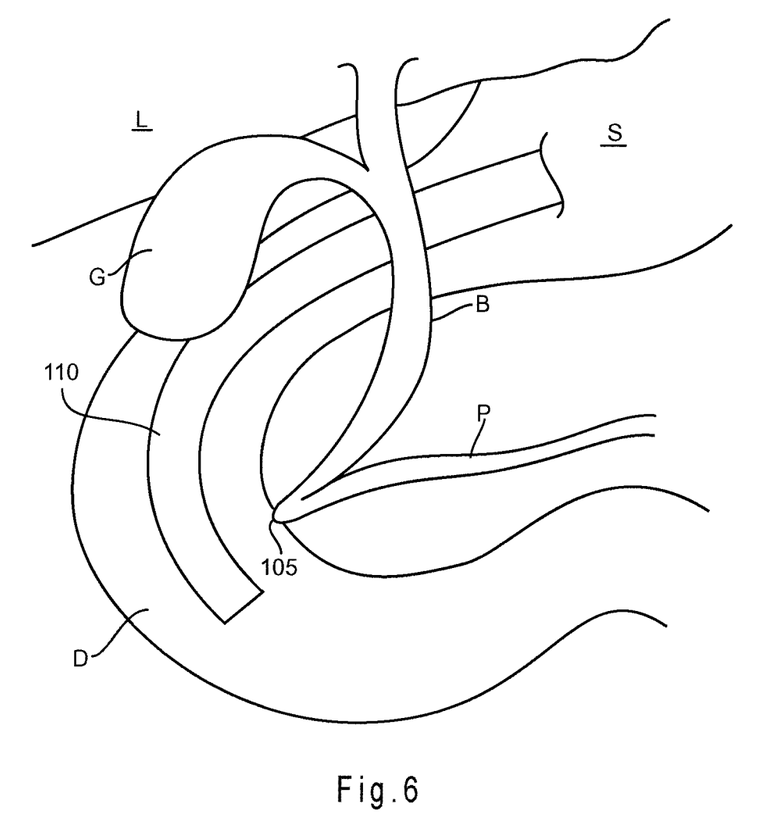
FIG. 6 is a schematic of a patient's anatomy in the vicinity of the papilla of Vater.
Figure 7A:
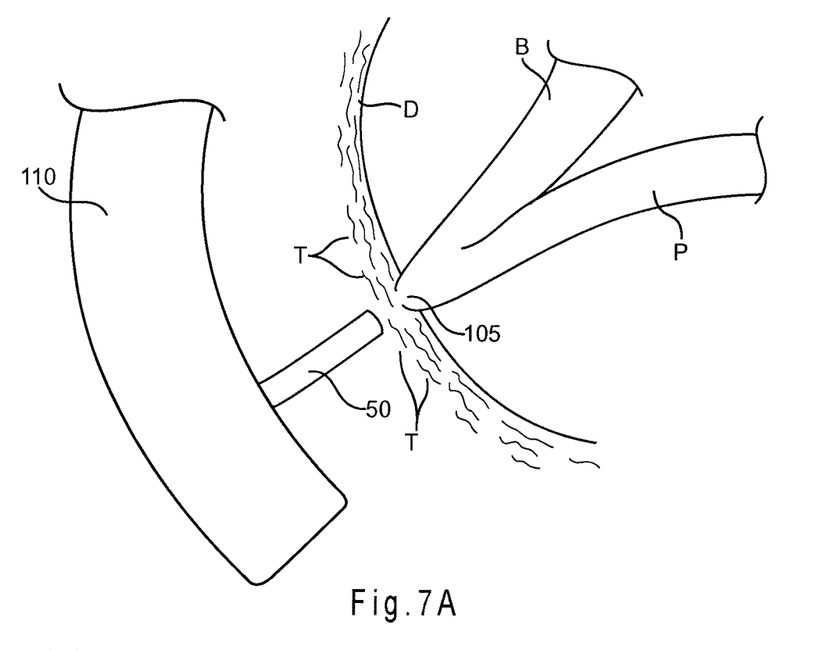
FIGS. 7A-7D describe method steps for using the spreader of FIGS. 1A-1B.

As mentioned above, spreader 20 may be used to spread tissue in the vicinity of a bodily opening to facilitate access into the opening. In FIGS. 6-7D, one exemplary use of spreader 20 is described, whereby spreader 20 facilitates access into the common bile duct via the papilla of Vater during an ERCP procedure.

As shown in FIG. 6, the pertinent anatomy depicts common bile duct B leading from liver L into duodenum D. Bile duct B joins with pancreatic duct P just before papilla of Vater 105, as shown in FIG. 6. Papilla of Vater 105 is a small opening in duodenum D that drains the secretions from bile duct B and pancreatic duct P. Stomach S also empties into duodenum D, as shown in FIG. 6.

During a first step of an ERCP procedure, endoscope 110 is inserted into a patient's mouth, through the esophagus, through stomach S, and into duodenum D, as schematically shown in FIG. 6. In a preferred embodiment, endoscope 110 is a side-viewing endoscope. The distal end of endoscope 110 is positioned in the vicinity of papilla of Vater 105. Papilla of Vater 105 may be located by visualizing the pancreas (not shown), and then tracing bile duct B and/or pancreatic duct P to the wall of duodenum D and papilla of Vater 105.

It may be difficult to gain and/or maintain access to bile duct B during an ERCP procedure for various reasons. First, accessing the small opening in papilla of Vater 105 may be troublesome. For example, the papillar opening may be fully or partially covered by soft tissue T, as shown in FIG. 7A. Further, even when cannulation through the papilla is achieved, it is easier to access pancreatic duct P rather than bile duct B, which is slightly angled to the side, as depicted in FIG. 6. Therefore, in accordance with one aspect, spreader 20 may be provided to facilitate access into bile duct B during an ERCP procedure.

In FIG. 7A, endoscope 110 has been maneuvered into a patient's duodenum D and positioned in the vicinity of papilla of Vater 105, as explained above. Catheter 50 is advanced through a working lumen (not shown) of endoscope 110 and is positioned adjacent to papilla of Vater 105, as shown in FIG. 7A.

As explained above with respect to FIGS. 3-5, spreader 20 preferably is pre-loaded into lumen 56 of catheter 50. Lumen 56 constrains arms 22, 24 and 26 in a closed position such that the arms are adjacent to one another. In a preferred embodiment, spreader 20 is adapted to be deployed in a controlled manner using a retainer system comprising first and second retainers. The first retainer may comprise looped region 42 at the proximal region of spreader 20, while the second retainer may comprise wire 70 having hook member 72 (FIG. 3), or may comprise rod 80 having bore 85 (FIG. 4), or another retaining means. During delivery of catheter 50, the first and second retainers are coupled together to secure spreader 20 within lumen 56.

Figure 7B:
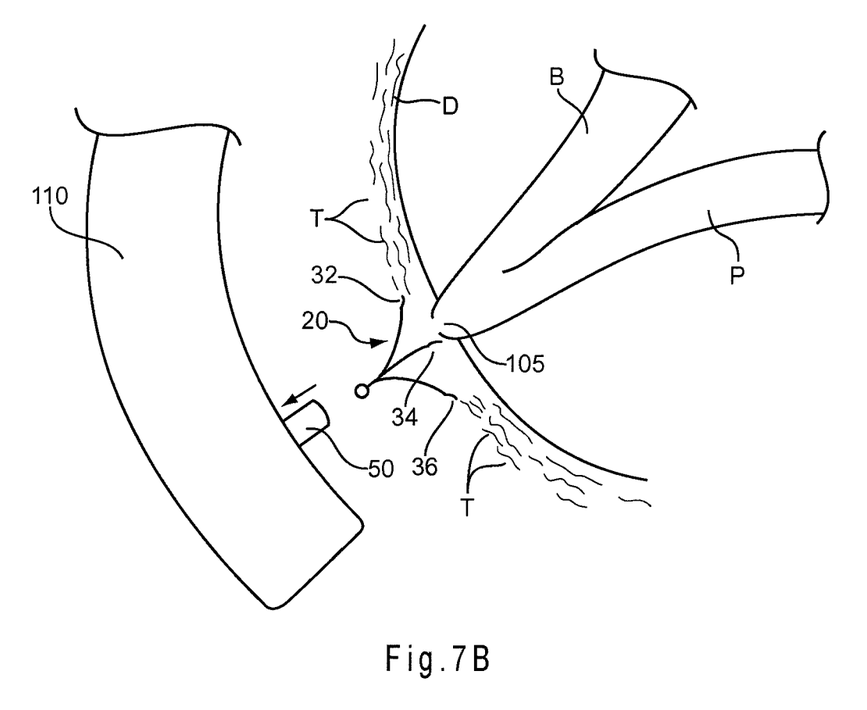

In a next step, shown in FIG. 7B, catheter 50 is retracted proximally with respect to spreader 20 so that engaging members 32, 34 and 36 of the arms of the spreader are exposed and no longer radially constrained. At this time, engaging members 32, 34 and 36 grasp tissue T in the vicinity of papilla of Vater 105 and urge tissue T in a radial direction away from the papillar opening, as depicted in FIG. 7B. Further retraction of catheter 50 causes the distal ends of arms 22, 24 and 26 to spread apart from one another. Preferably, prior to deployment of spreader 20, lumen 56 is aligned with papilla of Vater 105 so that when arms 22, 24 and 26 expand radially outward, they expand away from the papillar opening.

After deployment of arms 22, 24 and 26, catheter 50 may be further retracted with respect to spreader 20 to expose the coupling junction between the first and second retainers. In the embodiment of FIG. 3, catheter 50 is retracted proximal to hook member 72, allowing looped region 42 of spreader 20 to be released from wire 70. In the embodiment of FIG. 4, catheter 50 is retracted proximal to bore 85, allowing looped region 42 of spreader 20 to be released from rod 80. Therefore, spreader 20 is left securely in place in front of papilla of Vater 105.

Figure 7C:
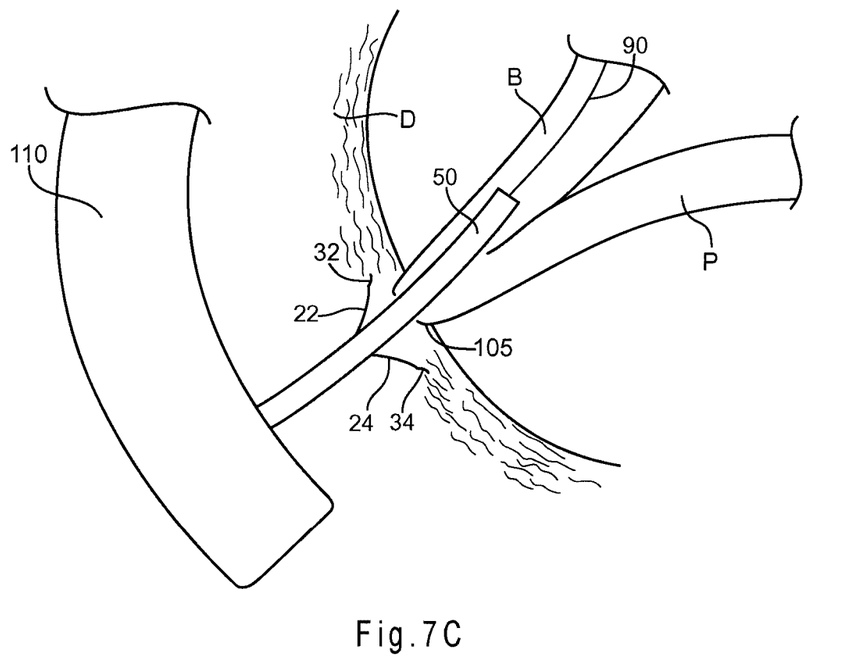
Figure 7D:
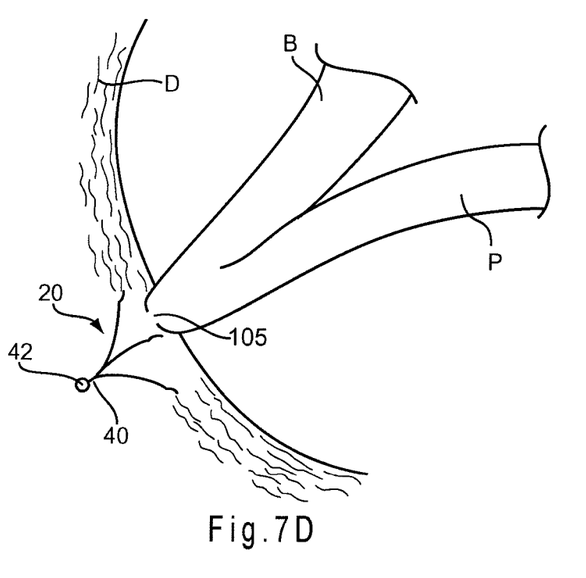

Referring now to FIG. 7C, in a next step wire guide 90 may be advanced distally between one or more arms 22, 24 and 26 of spreader 20 and guided into bile duct B. Wire guide 90 may be advanced through a dedicated wire guide lumen of catheter 50, such as lumen 52 of FIG. 3. Subsequently, catheter 50 may be advanced distally over wire guide 90, between one or more arms 22, 24 and 26 of spreader 20, and into bile duct B, as shown in FIG. 7C (in this illustration, it should be noted that arm 26 is obscured by catheter 50).

Advantageously, since the arms of spreader 20 hold tissue T in a spread position away from papilla of Vater 105, it may be easier for endoscope 110 to view the papillar opening. Therefore, it may be easier to cannulate papilla of Vater 105 and achieve access into bile duct B. Importantly, the likelihood of entering and damaging pancreatic duct P may be reduced.

If desired, one or more procedures may be performed while catheter 50 is disposed within bile duct B. For example, an extraction basket (not shown) may be advanced through catheter lumen 54 and used to remove a gallstone lodged within bile duct B. Alternatively, as mentioned above, catheter 50 may be used to treat a biliary stricture, for example, by disposing an inflation balloon on an exterior surface of catheter 50. Further, a lithotripsy probe or other device may be inserted into bile duct B via the papillar opening once access is achieved and maintained.

Once the desired surgical procedure(s) are completed, spreader 20 may be left inside the patient or removed. In order to remove spreader 20, a reverse sequence of one or more steps from 7A-7B may be used. For example, the hook member 72 on the distal end of wire 70 may be advanced and engaged with the looped region 42 of spreader 20. Catheter 50 is then advanced distally such that lumen 56 is advanced over proximal region 40 of spreader 20 to collapse the arms 22, 24 and 26 together, thereby allowing spreader 20 to be removed. Alternatively, a forceps or other grasping device can be deployed through a separate sheath, the forceps being used to grasp and pull the spreader 20 into the sheath. The catheter or sheath is advanced over proximal region 40 and then over arms 22, 24 and 26 to cause the arms to move radially inward and disengage tissue T. The advancement of the catheter or sheath will cause arms 22, 24 and 26 to be radially constrained therein. If desired, spreader 20 may be retracted proximally within the catheter or sheath by engaging looped region 42.

Alternatively, spreader 20 may be left inside the patient, as shown in FIG. 7D. Spreader 20 may be configured to detach from tissue T over a period of time and may pass naturally through the patient. Spreader 20 may also comprise a biodegradable material that will eventually dissolve and pass harmlessly out of the body. If desired, spreader 20 may be designed to permanently engage tissue T, in which case the spreader will be left inside the patient.

In a further alternative embodiment, spreader 20 may be removable when made from a shape memory material, whereby the spreader can assume a relaxed configuration in which it readily disengages from tissue upon application of a certain cold or hot medium. More specifically, a shape memory material may undergo a substantially reversible phase transformation that allows it to "remember" and return to a previous shape or configuration. For example, in the case of nickel-titanium alloys, a transformation between an austenitic phase and a martensitic phase may occur by cooling and/or heating (shape memory effect) or by isothermally applying and/or removing stress (superelastic effect). Austenite is characteristically the stronger phase and martensite is the more easily deformable phase.

In an example of the shape memory effect, a nickel-titanium alloy having an initial configuration in the austenitic phase may be cooled below a transformation temperature ($M_f$) to the martensitic phase and then deformed to a second configuration. Upon heating to another transformation temperature ($A_f$), the material may spontaneously return to its initial configuration. Generally, the memory effect is one-way, which means that the spontaneous change from one configuration to another occurs only upon heating. However, it is possible to obtain a two-way shape memory effect, in which a shape memory material spontaneously changes shape upon cooling as well as upon heating.

Applying these shape-memory properties to spreader 20, it will be possible to retract catheter 50 to expose spreader 20 to body temperature and cause arms 22, 24 and 26 to expand radially outward and grasp tissue. When it is desired to remove spreader 20, a second, predetermined temperature may be applied to spreader 20, e.g., by injecting fluid through catheter 50 or by direct contact of a temperature-inducing element, to cause arms 22, 24 and 26 to transform to a relaxed state in which they more easily let go of the tissue. Upon application of this temperature, spreader 20 may assume a relatively atraumatic posture so that it can be safely passed through the body.

Figure 8:
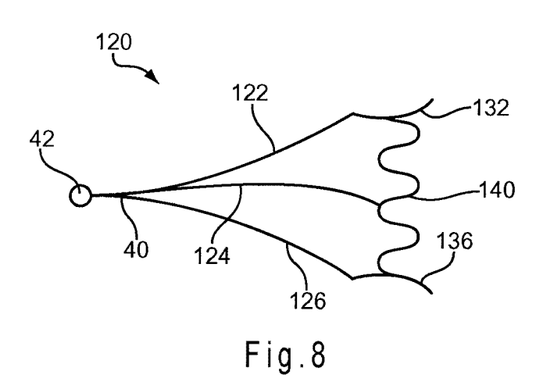
FIG. 8 is an alternative embodiment of the device of FIGS. 1A-1B.

Referring now to FIG. 8, an alternative spreader is described. Spreader 120 is similar to spreader 20 of FIGS. 1-7, with a main exception that biasing member 140 is added. As shown in FIG. 8, biasing member 140 may be coupled directly to engaging members 132 and 136 of arms 122 and 126, respectively. Biasing member 140 also may be coupled directly to arms 122, 124 and/or 126 at a location proximal of the engaging members. As depicted, biasing member 140 may comprise a cylindrical, zig-zag shaped member having a plurality of substantially straight sections separated by a plurality of bends, although other configurations are possible. Biasing member 140 may be manufactured using a nickel-titanium alloy and may comprise a reduced profile delivery configuration and a radially expanded spreading configuration. In the expanded state, biasing member 140 may provide a larger tissue engaging area compared to the use of arms 22, 24 and 26 by themselves, and may facilitate entry into bodily openings that are otherwise difficult to access.

While reference has been made to facilitating access to the common bile duct via the papilla of Vater, spreader 20 may be used to help spread tissue to gain access to many other constrained bodily openings, passageways, ducts or cavities. Alternatively, spreader 20 may be used to open an annular passageway itself, as opposed to tissue in the vicinity of the passageway. In the latter embodiment, arms 22, 24 and 26 may be designed to have a stronger radial force, for example, to spread open a sphincter, such as the sphincter of Oddi or another passageway.

Figure 9:
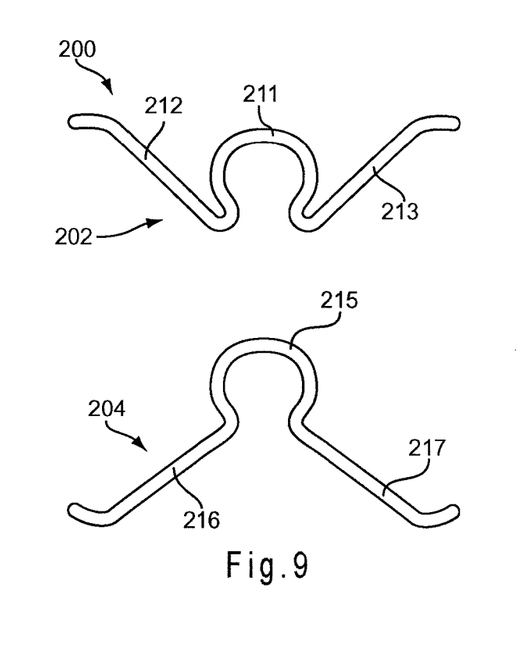
FIG. 9 is a top view illustrating a further alternative embodiment of the device of FIGS. 1A-1B.

Referring now to FIGS. 9-14, further alternative embodiments of a spreader are described. In FIG. 9, spreader 200 is formed from first and second portions 202 and 204. First portion 202 comprises first and second arms 212 and 213, which are separated by central region 211. Similarly, second portion 204 comprises third and fourth arms 216 and 217, which are separated by central region 215, as shown in FIG. 9. The four arms 212, 213, 216 and 217 may be provided as generally explained above with respect to the arms 22, 24 and 26 of spreader 20. In particular, each of the four arms 212, 213, 216 and 217 may comprise a curvature and/or an engaging member bent outwardly and adapted to grasp tissue.

In a preferred embodiment, central regions 211 and 215 may comprise a wire or other suitable material bent into a substantially circumferential shape spanning between 180-

360 degrees. Alternatively, central regions 211 and 215 may comprise a wire forming a 360 degree loop, U-shape, or the like, for purposes described below.

Figure 10:
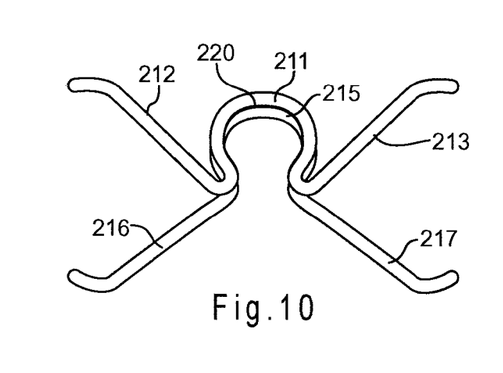
FIG. 10 is a top view of the device of FIG. 9 in an assembled state.
Figure 11:
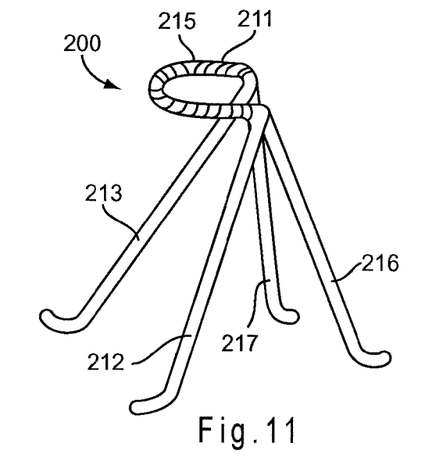
FIG. 11 is an elevated side view of the device of FIG. 9 in an assembled state.

Referring to FIGS. 10-11, in a next step, first and second portions 202 and 204 are coupled together. In FIG. 10, central regions 211 and 215 may be aligned and then coupled together using an adhesive 220. Once coupled, the four arms 212, 213, 216 and 217 of spreader 200 preferably extend in opposing circumferential directions to facilitate spreading tissue, as explained above. Alternatively, as shown in FIG. 11, central regions 211 and 215 may be braided or twisted together. In either of the embodiments shown in FIGS. 10-11, the overlapping portions may form a loop, U-shape, or the like. In a further alternative embodiment, a sleeve may be disposed over central regions 211 and 215 to help secure first and second portions 202 and 204 together.

Figure 12:
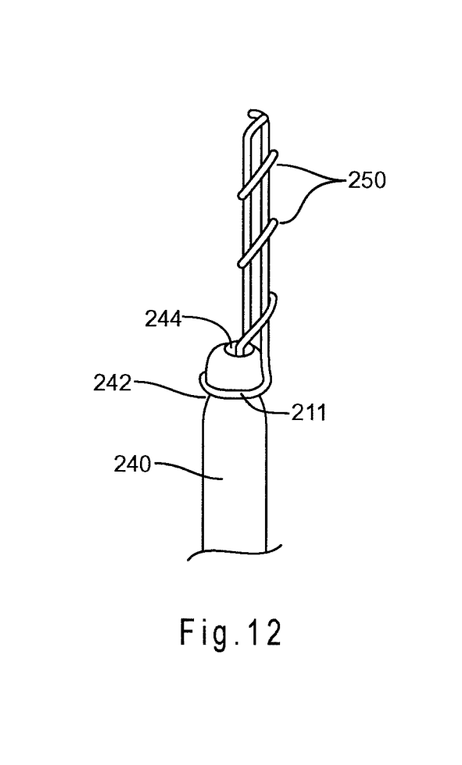
FIG. 12 is a side view of apparatus suitable for delivering the device of FIGS. 9-11.

Referring now to FIG. 12, a catheter suitable for delivering spreader 200 is described. Catheter 240 preferably comprises proximal and distal ends and at least one lumen 244 extending therebetween. Catheter 240 further comprises an exterior surface having at least one ridge 242 formed therein, as shown in FIG. 12. In this embodiment, spreader 200 is delivered substantially from the outside of catheter 240, as opposed to through an interior lumen. Specifically, overlapping central regions 211 and 215 may be disposed around a perimeter of catheter 240 using a frictional fit, or by being held into place within ridge 242, or using an additional securing mechanism.

In FIG. 12, at least one filament 250 is employed to hold the four arms 212, 213, 216 and 217 of spreader 200 together in the delivery state. Filament 250 preferably extends through lumen 244 and spans the entire length of catheter 240. Once spreader 200 is positioned at a desired location, a proximal end of filament 250 is retracted proximally to thereby release arms 212, 213, 216 and 217 and allow their radial expansion, as shown in FIGS. 10-11 above.

Figure 13:
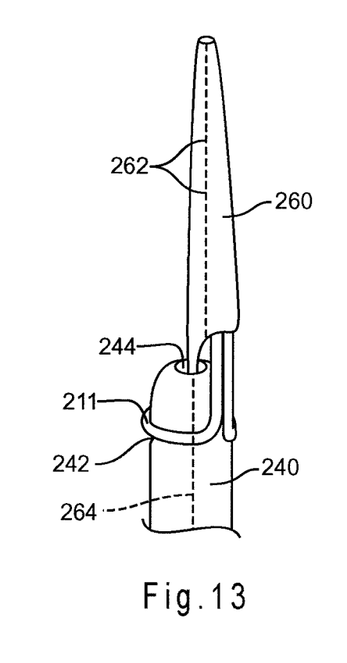
FIG. 13 is a side view of an alternative apparatus suitable for delivering the device of FIGS. 9-11.

In an alternative embodiment, shown in FIG. 13, a splittable sheath is employed to hold the four arms 212, 213, 216 and 217 of spreader 200 together in the delivery state. Splittable sheath 260 has a proximal end coupled to wire 264, which extends longitudinally through lumen 244. Splittable sheath 260 further comprises at least one tear line 262. In use, when it becomes desirable to deploy spreader 200, wire 264 is retracted proximally within lumen 244, thereby causing the at least one tear line 262 to tear apart and release spreader 200. At this time, splittable sheath 260 may be withdrawn into lumen 244, while arms 212, 213, 216 and 217 are released and radially expand to engage tissue, as depicted in FIGS. 10-11 above.

Figure 14:
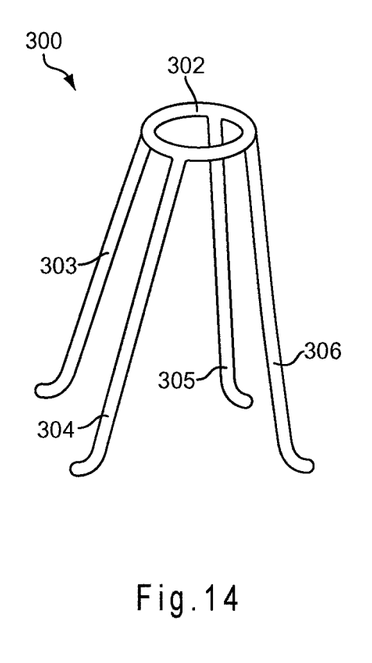
FIG. 14 is a perspective view of a further alternative embodiment of the device of FIGS. 1A-1B.

Referring to FIG. 14, in a farther alternative embodiment, spreader 300 is similar to spreader 200 of FIGS. 9-11, with a main exception that it is manufactured from a single component instead of two separate components that are coupled together. Spreader 300 comprises a base portion 302 having a circular configuration, and a plurality of integral arms 303-306 extending therefrom, as shown in FIG. 14. Base portion 302 may be sized to be fit over an outer surface of catheter 240, for example, using a frictional fit, or by being placed in ridge 242. Alternatively, spreader 300 may be configured for delivery internally though a lumen of a catheter, as generally described above with respect to FIGS. 3-4.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

I claim:

1. Apparatus for facilitating entry through a bodily opening, the apparatus comprising:
    a spreader having a proximal region and a plurality of arms, each of the arms having a proximal end and a distal end, wherein the proximal end of each of the arms is joined to the proximal region of the spreader and extends distally therefrom, each of the arms being formed of a resilient material and shaped so that the distal ends tend to be spaced apart from each other when the spreader is in an open position and adjacent to each other when the spreader is in a closed position; and
    at least one engaging member disposed near the distal end of each arm, each engaging member adapted to grasp tissue,
    wherein a transformation of the spreader from the closed position to the open position is adapted to spread tissue in the vicinity of the bodily opening,
    wherein the spreader has a deployed state in which it remains engaged with the tissue in the open position.

2. The apparatus of claim 1 wherein the engaging member comprises at least one barb.

3. The apparatus of claim 1 wherein the engaging member comprises a roughened surface.

4. The apparatus of claim 1 further comprising a catheter having proximal and distal ends and a first lumen disposed between therebetween, wherein the first lumen is adapted to receive the spreader and constrain the arms of the spreader in the closed position.

5. The apparatus of claim 4 wherein the catheter comprises an outer diameter configured to allow the catheter to be advanced between at least two of the arms of the spreader when the spreader is in the open position.

6. The apparatus of claim 4 wherein the arms of the spreader are adapted to be transformed from the open position to the closed position when the catheter is advanced distally over the arms.

7. The apparatus of claim 1 further comprising:
    a first retainer disposed near the proximal region of the spreader; and
    a second retainer adapted to be coupled to the first retainer prior to deployment of the spreader, and further configured to be disengaged from the first retainer after the spreader is deployed.

8. The apparatus of claim 7 wherein one of the first retainer and the second retainer comprises a looped region and the other comprises a hook member.

9. The apparatus of claim 1 wherein the spreader comprises a shape memory property to facilitate removal of the spreader from engagement to the tissue upon exposure of a predetermined temperature to the spreader.

10. Apparatus for facilitating entry through a bodily opening, the apparatus comprising:
    a spreader having a proximal region and a plurality of arms, each of the arms having a proximal end and a distal end, wherein the proximal end of each of the arms is joined to a first retainer and extends distally therefrom, each of the arms being formed of a resilient material and shaped so that the distal ends tend to be spaced apart from each other when the spreader is in an open position and adjacent to each other when the spreader is in a closed position;
    at least one engaging member disposed near the distal end of each arm, each engaging member adapted to grasp tissue situated in the vicinity of the bodily opening;

a second retainer adapted to be coupled to the first retainer prior to deployment of the spreader, and further configured to be disengaged from the first retainer after the spreader is deployed; and a catheter having proximal and distal ends and a first lumen disposed therebetween, wherein the first lumen is adapted to receive the spreader and constrain the arms of the spreader in the closed position, wherein the catheter comprises an outer diameter configured to allow the catheter to be advanced between at least two of the arms of the spreader when the spreader is in the open position, and wherein the spreader has a deployed state in which it remains engaged with the tissue in the open position.

11. The apparatus of claim 10 wherein a transformation of the spreader from the closed position to the open position is adapted to spread tissue in the vicinity of the bodily opening.

12. The apparatus of claim 10 wherein the arms of the spreader are adapted to be transformed from the open position to the closed position when the catheter is advanced distally over the arms.

13. The apparatus of claim 10 wherein one of the first retainer and the second retainer comprises a looped region and the other comprises a hook member.

14. The apparatus of claim 10 wherein the second retainer comprises a wire having proximal and distal ends and a hook member disposed at the distal end, wherein the hook member is adapted to be disposed through a loop member on the spreader prior to deployment of the spreader.

15. The apparatus of claim 10 wherein the second retainer comprises a rod having proximal and distal ends and a bore disposed near the distal end, wherein a looped member on the spreader is adapted to be disposed at least partially through the bore prior to deployment of the spreader.

* * * * *